US012668805B2

(12) United States Patent　　(10) Patent No.:　US 12,668,805 B2
Bie et al.　　(45) Date of Patent:　Jun. 30, 2026

(54) GENE FOR BOOSTING GENETIC TRANSFORMATION EFFICIENCY OF WHEAT AND USE THEREOF

(71) Applicant: Shandong Agricultural University, Tai'an City (CN)

(72) Inventors: Xiaomin Bie, Tai'an City (CN); Xiansheng Zhang, Tai'an City (CN); Menglu Li, Tai'an City (CN); Xiaoting Shi, Tai'an City (CN); Ying Song, Tai'an City (CN); Mei Yu, Tai'an City (CN)

(73) Assignee: SHANDONG AGRICULTURAL UNIVERSITY, Tai'an City (CN)

( * ) Notice: Subject to any disclaimer, the term of this patent is extended or adjusted under 35 U.S.C. 154(b) by 0 days.

(21) Appl. No.: 19/010,669

(22) Filed: Jan. 6, 2025

(65) Prior Publication Data

US 2026/0117239 A1　　Apr. 30, 2026

(30) Foreign Application Priority Data

Oct. 30, 2024　　(CN) ......................... 202411526588.4

(51) Int. Cl.
　　*C12N 15/82*　　(2006.01)
　　*C07K 14/415*　　(2006.01)
(52) U.S. Cl.
　　CPC ........ *C12N 15/8205* (2013.01); *C07K 14/415* (2013.01); *C12N 15/8216* (2013.01); *C07K 2319/20* (2013.01)
(58) Field of Classification Search
　　CPC ............ C12N 15/8205; C12N 15/8216; C07K 14/415; C07K 2319/20
　　See application file for complete search history.

(56) References Cited

U.S. PATENT DOCUMENTS

2022/0356481 A1* 11/2022 Sun ...................... C07K 14/415

OTHER PUBLICATIONS

Wang, W., Wu, Y., Shi, R., Sun, M., Li, Q., Zhang, G., Wu, J., Wang, Y., & Wang, W. (2020). Overexpression of wheat α-mannosidase gene TaMP impairs salt tolerance in transgenic Brachypodium distachyon. Plant cell reports, 39(5), 653-667.*
Wang, K., Shi, L., Liang, X et al. The gene TaWOX5 overcomes genotype dependency in wheat genetic transformation. Nat. Plants 8, 110-117 (2022).*
International Brachypodium Initiative (2010). Genome sequencing and analysis of the model grass Brachypodium distachyon. Nature, 463(7282), 763-768.*

Koppolu, R., Chen, S., & Schnurbusch, T. (2022). Evolution of inflorescence branch modifications in cereal crops. Current Opinion in Plant Biology, 65, 102168.*
Wang, D., Guo, Y., Liu, M., & Liu, H. (2025). The function of TaWOX14 in wheat genetic transformation. Plant cell reports, 44(8), 176.*
Li, Y., Chu, L., Lyu, P., Lyu, W., Xie, P., Zhang, C., . . . & Zhao, T. (2024). Mutations in the WUSCHEL-related homeobox1 gene cause an increased leaflet number in soybean. The Crop Journal, 12(6), 1645-1654.*
Li, Juanjuan, and Yue Zhang. "The Tissue Expression Divergence of the WUSCHEL-Related Homeobox Gene Family in the Evolution of Nelumbo." Plants 14.13 (2025): 1909.*
Thompson, C. J., Mowa, N. R., Tizard, R., Crameri, R., Davies, J. E., Lauwereys, M., & Botterman, J. (Sep. 1987). Characterization of the herbicide-resistance gene bar from Streptomyces hygroscopicus. The EMBO journal, 6(9), 2519-2523.
BlpR. (Accessed Mar. 5, 2026). https://www.molecularcloud.org/part/BlpR/402.html.
Altschul, S. F., Gish, W., Miller, W., Myers, E. W., & Lipman, D. J. (Oct. 1990). Basic local alignment search tool. Journal of molecular biology, 215(3), 403-410.
Karlin, S., & Altschul, S. F. (Jun. 1993). Applications and statistics for multiple high-scoring segments in molecular sequences. Proceedings of the National Academy of Sciences, 90(12), 5873-5877.
Sambrook, J., Fritsch, E. E., & Maniatis, T. (Jan. 2001). Molecular Cloning, A laboratory Manual, Second Edition., Cold Spring Harbor Laborotory.
Spector, D. L., Goldman, R. D., & Leinwand, L. A. (Jan. 1998). Cells: a laboratory manual (vol. 1). Cold Spring Harbor Laboratory Press.
Ishida, Y., Tsunashima, M., Hiei, Y., & Komari, T. (Sep. 2014). Wheat (Triticum aestivum L.) transformation using immature embryos. In Agrobacterium protocols: vol. 1 (pp. 189-198). New York, NY: Springer New York.
Sambrook, J. & Russel, D.W. (Jan. 2001). Guide to Molecular Cloning Experiments, Third Edition. (vol. 1). Cold Spring Harbor Laboratory Press.

\* cited by examiner

*Primary Examiner* — Bratislav Stankovic
*Assistant Examiner* — George W Meyer
(74) *Attorney, Agent, or Firm* — Tutunjian & Bitetto, P.C.

(57)　　ABSTRACT

Disclosed is a gene for boosting genetic transformation efficiency of wheat and use thereof, which belongs to the field of plant genetic engineering technology. The use of a TaHRF1 gene and an encoded protein thereof can promote integration of an exogenous nucleic acid molecule into a genome of a plant of interest, and boost efficiency of the integration of the nucleic acid molecule, and the transformed plant grows and develops normally. The plant of interest includes, but is not limited to, monocotyledonous plants such as wheat. The present disclosure provides a new and important genetic resource for overcoming the genotype dependence in genetic transformation of wheat.

2 Claims, 5 Drawing Sheets
Specification includes a Sequence Listing.

GENE FOR BOOSTING GENETIC TRANSFORMATION EFFICIENCY OF WHEAT AND USE THEREOF

CROSS REFERENCE TO RELATED APPLICATION

This patent application claims the benefit and priority of Chinese Patent Application No. 202411526588.4 filed with the China National Intellectual Property Administration on Oct. 30, 2024, the disclosure of which is incorporated by reference herein in its entirety as part of the present application.

REFERENCE TO SEQUENCE LISTING

A computer readable XML file entitled "GWP20241107299", that was created on Dec. 16, 2024, with a file size of about 18,046 bytes, contains the sequence listing for this application, has been filed with this application, and is hereby incorporated by reference in its entirety.

TECHNICAL FIELD

The present disclosure relates to the field of plant genetic engineering technology, and particularly to a gene for boosting the genetic transformation efficiency of wheat and use thereof.

BACKGROUND

Wheat is an important food crop in the world, and the high yield, high quality, stable production and high efficiency production of wheat are closely related to secure supply of food, social and economic stability, and human nutrition and health. Wheat breeding is the main technical means to achieve the high yield, high quality, stable production and high efficiency production of wheat. Genetic transformation technology and gene editing are important technical means to improve agronomic traits such as crop yield, disease resistance and quality, and have achieved great success in crops such as soybean, maize, cotton and rapeseed. In contrast, wheat is an allohexaploid plant, with a large genome and many repeat sequences, poor regeneration capacity and relatively difficult genetic transformation, which have become the main causes for the slow progress of bio-breeding of wheat.

People have attempted to introduce an exogenous gene into a target plant using various transformation methods such as a gene gun bombardment method, an *Agrobacterium*-mediated method, a pollen tube pathway method, an ultrasonic method, an ion beam implantation method, a laser microbeam puncture method, and a Polyethylene glycol (PEG) method. The *Agrobacterium*-mediated method is currently the most commonly used method for wheat transformation. The main type of *Agrobacterium* is *Agrobacterium tumefaciens*. This method has the advantages of low cost, simple operation, high efficiency of introducing exogenous genes, low copy number, good genetic stability, etc. The gene gun bombardment method is a physical transformation method, in which an exogenous gene is introduced into organisms by physical means of high-speed particle bombardment, which has the advantages of being genotype-independent and direct transformation, and is also one of the commonly used transformation methods.

The type of explant for plant genetic transformation is also an important factor affecting transformation efficiency.

Currently, commonly used explants mainly include immature embryo, mature embryo, anther-derived callus and young ear. In general, explants taken from young and early-stage parts of plants have stronger regeneration and transformation capacity.

In recent years, great breakthroughs have been made in wheat genetic transformation technology. Overexpression of key genes that promote regeneration can enhance the regeneration capacity and boost the transformation efficiency of crops. A new method for boosting the genetic transformation efficiency of wheat has gradually gained recognition among people. However, the number of regeneration-related genes that have been isolated is still relatively small. Therefore, further isolation and identification of key genes that promote wheat regeneration is of great importance for improving agronomic traits of crops and promoting biotechnological breeding.

SUMMARY

Aiming at the prior art described above, an objective of the present disclosure is to provide a gene for boosting the genetic transformation efficiency of wheat and use thereof. It has been found through research in the present disclosure that: The overexpression of a TaHRF1 gene of wheat significantly boosts the transformation efficiency of a plurality of wheat varieties, effectively overcoming the genotype dependence of wheat. The use of TaHRF1 can improve the genetic transformation efficiency of plants. Moreover, by using TaHRF1 as a transformation-assisting gene, the genetic transformation efficiency of crops such as wheat can be boosted and the cost of genetic transformation can be reduced, providing solid fundamental technical support for biotechnological breeding.

In order to achieve the objective described above, the present disclosure adopts the following technical solutions.

In a first aspect of the present disclosure, provided is use of a TaHRF1 gene in (1) or (2) as follows:
- (1) boosting transformation efficiency of integration of a nucleic acid molecule into a genome of wheat;
- (2) boosting regeneration efficiency of a wheat plant by stable expression of a nucleic acid molecule.

The TaHRF1 gene is a nucleic acid molecule as shown in i) or ii) or iii) below:
- i) a nucleic acid molecule having a nucleotide sequence set forth in SEQ ID NO. 1;
- ii) a nucleic acid molecule having 80% or more homology with the nucleotide sequence of i) and expressing a protein of the same or similar function, and a corresponding allele, homologous gene, mutant gene and derived gene;
- iii) a nucleic acid molecule encoding an amino acid sequence set forth in SEQ ID NO. 2, excluding i).

The nucleic acid molecule may be DNA, such as cDNA, genomic DNA or recombinant DNA; the nucleic acid molecule may also be RNA, such as mRNA or hnRNA.

The term "homology" used herein refers to sequence similarity to a natural nucleic acid sequence. Homology can be evaluated using computer software. For example, it can be determined using the BLAST algorithm (Altschul et al., 1990. Journal of Molecular Biology 215:403-410; Karlin and Altschul., 1993. Proceedings of the National Academy of Sciences 90:5873-5877).

In the nucleic acid molecules described above, the 80% or more homology may be at least 80%, 85%, 90%, 95%, 96%, 98% or 99% homology.

In a second aspect of the present disclosure, provided is use of a protein encoded by a TaHRF1 gene in (1) or (2) as follows:

(1) boosting transformation efficiency of integration of a nucleic acid molecule into a genome of wheat;

(2) boosting regeneration efficiency of a wheat plant by stable expression of a nucleic acid molecule.

Preferably, the protein encoded by the TaHRF1 gene is as shown in any one of (A1) or (A2) or (A3) below:

(A1) a protein consisting of an amino acid sequence set forth in SEQ ID NO. 2 of the Sequence Listing;

(A2) a fusion protein obtained by attaching a protein tag to the N-terminus and/or the C-terminus of the protein defined in (A1).

(A3) an encoded protein similar to the protein set forth in SEQ ID NO. 2, or a protein obtained by a substitution, deletion or insertion of one, several or tens of amino acids.

The proteins of (A1), (A2) and (A3) can be synthesized artificially or obtained by first synthesizing encoding genes thereof and then performing biological expression.

In the proteins described above, the protein tag refers to a polypeptide or protein that is fused and expressed with a protein of interest using in-vitro DNA recombination techniques, so as to facilitate expression, detection, tracing and/or purification of the protein of interest. In order to facilitate the purification of the protein in (A1), a tag can be attached to the amino terminus or the carboxyl terminus of the protein in (A1). The tag may be Poly-Arg (typically six Arg, RRRRRR (SEQ ID NO:11)), Poly-His (typically six His, HHHHHH (SEQ ID NO:12)), FLAG (DYKDDDDK (SEQ ID NO:13)), Strep-tag II (WSHPQFEK (SEQ ID NO:14)) or c-Myc (EQKLISEEDL (SEQ ID NO:15)).

In a third aspect of the present disclosure, provided is use of an expression cassette, recombinant expression vector or recombinant bacterium containing a TaHRF1 gene in (1) or (2) as follows:

(1) boosting transformation efficiency of integration of a nucleic acid molecule into a genome of wheat;

(2) boosting regeneration efficiency of a wheat plant by stable expression of a nucleic acid molecule.

The recombinant expression vector can be constructed using existing plant expression vectors. Preferably, a recombinant expression vector containing a TaHRF1 gene is constructed using a pc186 expression vector.

In a fourth aspect of the present disclosure, provided is a method for boosting transformation efficiency of introduction of a nucleic acid molecule into a plant of interest, the method including the following step:

transforming a TaHRF1 gene and a target nucleic acid molecule into a plant of interest to achieve the purpose of boosting transformation efficiency of introduction of the target nucleic acid molecule into the plant of interest.

The TaHRF1 gene is a nucleic acid molecule as shown in i) or ii) or iii) below:

i) a nucleic acid molecule having a nucleotide sequence set forth in SEQ ID NO. 1;

ii) a nucleic acid molecule having 80% or more homology with the nucleotide sequence of i) and expressing a protein of the same or similar function, and a corresponding allele, homologous gene, mutant gene and derived gene;

iii) a nucleic acid molecule encoding an amino acid sequence set forth in SEQ ID NO. 2, excluding i).

In the method described above, the TaHRF1 gene and the target nucleic acid molecule can be transformed into the plant of interest by one vector or by different vectors.

In some embodiments, the TaHRF1 gene and the target nucleic acid molecule are transformed into the plant of interest by a pc186 expression vector.

In the method described above, the plant of interest includes, but is not limited to, monocotyledonous plants such as wheat, maize, rice and barley, and can also be used in dicotyledonous plants such as soybean and rapeseed.

The present disclosure has the following beneficial effects.

It has been found for the first time in the present disclosure that a TaHRF1 gene can boost the transformation efficiency of integration of a target nucleic acid molecule into a plant of interest and/or promote the integration of the nucleic acid molecule into the plant of interest. The plant of interest includes, but is not limited to, monocotyledonous plants such as wheat. An overexpression vector is constructed using a CDS sequence of the TaHRF1 gene, and introduced into an *Agrobacterium* strain, with which wheat immature embryo of different genotypes of wheat are infected. The results show that the overexpression vector of the TaHRF1 gene can promote the entry and integration of the target nucleic acid molecule into a genome of the plant of interest compared with a control vector. Using a TaHRF1 gene can boost the efficiency of the integration of a target gene into a genome of a plant, which in turn boosts the genetic transformation efficiency of monocotyledonous plants, especially wheat, and the genetically transformed plant grows and develops normally. The present disclosure has important economic and social benefits for accelerating plant genetic function research and improving agronomic traits of crops.

BRIEF DESCRIPTION OF THE DRAWINGS

FIG. 3A represents a callus transformed with the pc186-TaHRF1 vector, FIG. 3B represents resistant seedlings emerging from a callus transformed with the pc186-TaHRF1 vector, FIG. 3C represents a callus transformed with the control vector pc186-GUS, and FIG. 3D represents resistant seedlings emerging from a callus transformed with the control vector pc186-GUS.

FIG. 4A represents a callus transformed with the pc186-TaHRF1 vector, FIG. 4B represents resistant seedlings emerging from a callus transformed with the pc186-TaHRF1 vector, FIG. 4C represents a callus transformed with the control vector pc186-GUS, and FIG. 4D represents resistant seedlings emerging from a callus transformed with the control vector pc186-GUS;

Figure 6:
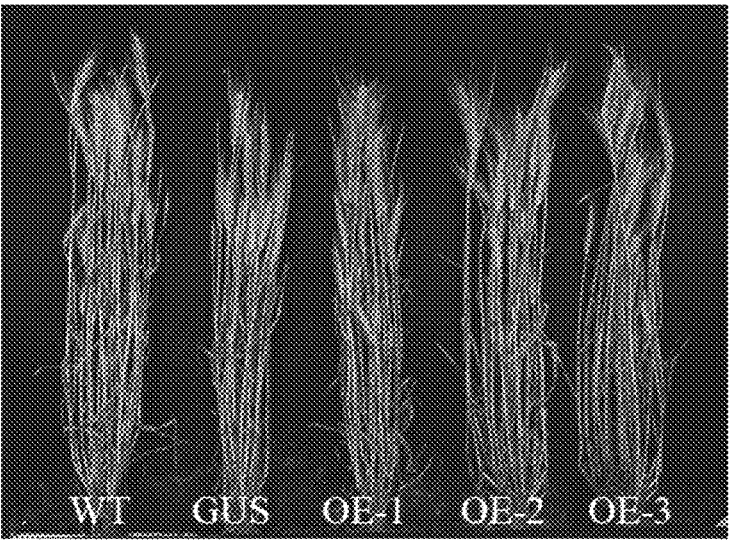

5 ing 66 after transformation, 9-14 represent candidate transgenic plants of Aifeng 3 after transformation, PC represents a positive plasmid, NC represents a negative control, WT represents a wild-type control, and M represents a 2000 bp molecular weight marker;

FIG. 6 shows that positive plants obtained by transforming Fielder with a plant expression vector pc186-TaHRF1 develop normally. WT represents a wild-type control, GUS represents a positive plant of a control vector pc186-GUS, and OE-1, OE-2 and OE-3 represent positive plants.

DETAILED DESCRIPTION OF THE EMBODIMENTS

It should be noted that following detailed description is exemplary and is intended to provide further illustration of the present application. Unless otherwise indicated, all technical and scientific terms used herein have the same meaning as commonly understood by those of ordinary skill in the art to which the present application belongs.

As mentioned earlier, due to the large and complex genome of wheat, the large number of repeat DNA sequences and the low regeneration capacity, the use of genetic transformation and gene editing techniques in wheat lags far behind other major crops. It has been found that the use of regeneration-related genes can promote the plant regeneration efficiency and genetic transformation efficiency in vitro tissue culture of wheat. However, the number of wheat regeneration-related genes that have been isolated and identified so far remains very small. There is a large difference in the transformation efficiency among different wheat genotypes, and most genotypes of the wheat cannot be transformed successfully. Moreover, the introduction of exogenous wheat regeneration genes may adversely affect the agronomic traits of wheat. Therefore, it is very difficult to explore wheat regeneration-related genes that are of practical value for production applications.

"Liangxing 66" is a wheat variety selected and bred by Shandong Liangxing Seed Industry Co., Ltd. using varieties Ji 91102/Ji 935031. It was approved on Dec. 13, 2010 by the Fourth Meeting of the Second National Crop Variety Approval Committee, with the approval number of Guoshen Mai 2010004. This variety has the characteristics of high yield, good quality, and high resistance to lodging, good yielding ability, wide adaptability to different regions, etc. "Aifeng 3" is a wheat variety selected and bred under the chairmanship of Academician ZHAO, Hong Zhang from Northwest A&F University. It is the first semi-dwarf variety popularized on a large scale in the history of wheat production in China. Both wheat varieties have been on the market for many years and are now facing the problem of further genetic improvement of the varieties.

However, "Liangxing 66" and "Aifeng 3" are among the most difficult wheat varieties to transform, making it difficult to undergo transgenic integration and gene editing.

Based on this, in-depth research has been conducted in the present disclosure on the genetic transformation of "Liangxing 66" and "Aifeng 3", and the results show that by transferring a TaHRF1 gene derived from wheat into the wheat varieties "Liangxing 66" and "Aifeng 3" using an *Agrobacterium*-mediated method, the genetic transformation efficiency of these two extremely difficult-to-transform wheat varieties can be significantly boosted.

In order to enable those skilled in the art to have a clearer understanding of the technical solutions of the present application, the technical solutions of the present application will be described in detail below in connection with specific examples.

The test materials used in the examples of the present disclosure, which are not specified, are conventional test materials in the field and are all commercially available. In the present disclosure, an expression vector is introduced into a plant cell. Methods of introduction are well known to those skilled in the art, including, but not limited to: an *Agrobacterium*-mediated method, a gene-gun bombardment method, an electroporation method, and an ovary injection method. A selectable marker gene used in the present disclosure is a bar gene, which encodes a phosphinothricin acetyltransferase PAT protein. Other selectable marker genes and reporter genes such as nptII and hpt can be further used. A screening antibiotic selected in the present disclosure is phosphinothricin, and screening agents such as bialaphos can also be selected to achieve the same effect. Where specific experimental conditions and methods are not indicated in the examples of the present disclosure, conventional conditions, such as those described in J. Sambrook et al., eds., Science Press, 2002, Molecular Cloning: A Laboratory Manual (Third Edition); D. L. Speckt et al., eds., Science Press, 2001, Cells: A Laboratory Manual; or conditions recommended by the manufacturer are generally followed.

Example 1: Cloning of a TaHRF1 Gene and Construction of Expression Vector

Calli formed after the induction of tissue culture from immature embryo explants of the wheat Fielder were collected. First, total RNA was extracted using an Ultrapure RNA Kit (Cwbiotech, catalog number: CW0581M). Subsequently, the extracted RNA was reverse transcribed into cDNA by referring to a FastKing RT Kit (With gDNase) kit (Tiangen Biotech (Beijing) Co., Ltd., catalog number: KR116).

The CDNA was amplified with primers (upstream primer: 5'-ATGCCGCAGACGCCATCGAC-3', SEQ ID NO. 3; downstream primer: 5'-CTAGTTTGTGGAGGTG-GAGCAA-3', SEQ ID NO. 4). An amplification system had a total volume of 25 μl, and included 2 μl of upstream primer (10 μmol/μl), 2 μl of downstream primer (10 μmol/μl), 12.5 μl of 2× Phanta Max Master Mix, 1 μl of cDNA template, and 7.5 μl of ddH₂O. Amplification conditions were: predenaturation at 95° C. for 3 minutes; denaturation at 95° C. for 15 seconds, annealing at 60° C. for 15 seconds, extension at 72° C. for 30 seconds, for 32 cycles; extension at 72° C. for 5 minutes; finally, holding at 16° C.

The amplified PCR product was ligated into a pEASY®-Blunt3 vector by referring to operation steps of a pEASY®-Blunt3 Cloning Kit (TransGen Biotech Co., Ltd., Beijing, catalog number: CB301-01) to obtain a pEASY-Blunt3-TaHRF1 vector, then Sanger sequencing was performed, and the results were analyzed.

Upon the sequencing analysis, the nucleotide sequence of the amplified PCR product was sequence 1 in the Sequence Listing, and the gene represented by the PCR product was named the TaHRF1 gene; the protein encoded by this gene was named TaHRF1, and the amino acid sequence of this protein was sequence 2 in the Sequence Listing, specifically as follows:

```
sequence 1 (SEQ ID NO. 1):
ATGCCGCAGACGCCATCGACCCGTTGGTGCCCGACGCCTGAGCAG

CTGATGATCCTGGAGGAGATGTACCGGAGCGGCGTGCGCACACCT
```

-continued

```
AACGCGGCGGAGATCCAGCAGATCACGGCGCACCTCGCCTACTAC

GGCCGCATCGAGGGAAAGAACGTCTTCTACTGGTTCCAGAACCAC

AAGGCCCGCGAGCGCCAGCGTCTCCGTCGCCGCCTCTGCGCCCGC

CACCAGCAACCCTCCTCCCCGGCGGCTCCTCCTCCTCCTCCTCCT

CCTCATACTGGTGCTGCCGGTGGCGGAGGCAATGCTGCTGGTGCT

GGTGCGGGCGTGAACGTGATGCACCCCGCGGTGATGCAGCTGCAC

CATCACCACCACACATACGCTACCAGCTGCTTCATGGCGCCTCAG

GGCTACTTGGAGCAGGAAACAGCAGCAGCAGGAGCTCTTCCAGTT

TCGGGGTTGGAGTTTGCAGGCAAGACAAGCCAGCAGCAGGAATGG

ATGGCGCAGGAGCAGATGGTGATGGAGAACAGCAACATTAACAAC

AGTGTAGCAGCAGCTGGAGGCAGCTCCGCATCGGCCGGCGGTGGT

ATGAATAATATGACCCCGCCGCCATGGCCATGCTGCCGGCCGCTC

AGAACCCTAGAGCTCTTCCCTACAAAGAGCACCGGTGGCGGCCTC

AGGGACGAGTGCAGCAGCTCCAAGTCCTCCTCTTGCTCCACCTCC

ACAAACTAG sequence 2 (SEQ ID NO. 2):
MPQTPSTRWCPTPEQLMILEEMYRSGVRTPNAAEIQQITAHLAYY

GRIEGKNVFYWFQNHKARERQRLRRRLCARHQQPSSPAAPPPPPP

PHTGAAGGGGNAAGAGAGVNVMHPAVMQLHHHHHTYATSCFMAPQ

GYLEQETAAAGALPVSGLEFAGKTSQQQEWMAQEQMVMENSNINN

SVAAAGGSSASAGGGMNNMTPPPWPCCRPLRTLELFPTKSTGGGL

RDECSSSKSSSCSTSTN
```

Sequence 1 can also be synthesized artificially and ligated into a pEASY-Blunt3 vector to obtain a pEASY-Blunt3-TaHRF1 vector.

Taking pEASY-Blunt3-TaHRF1 as a template, PCR amplification was performed with a primer pair designed (upstream primer: 5'-CACCATGCCGCAGACGCCATC-3', SEQ ID NO. 5; downstream primer: 5'-CTAGTTTGTG-GAGGTGGAGCAA-3', SEQ ID NO. 4). An amplification system consisted of 2 μl of upstream primer (10 μmol/μl), 2 μl of downstream primer (10 μmol/μl), 12.5 μl of 2× Phanta Max Master Mix, 1 μl of cDNA template, and a balance of ddH₂O to 25 μl. Amplification conditions were: predenaturation at 95° C. for 3 minutes; denaturation at 95° C. for 15 seconds, annealing at 58° C. for 15 seconds, extension at 72° C. for 30 seconds, for 32 cycles; extension at 72° C. for 5 minutes.

Figure 1:
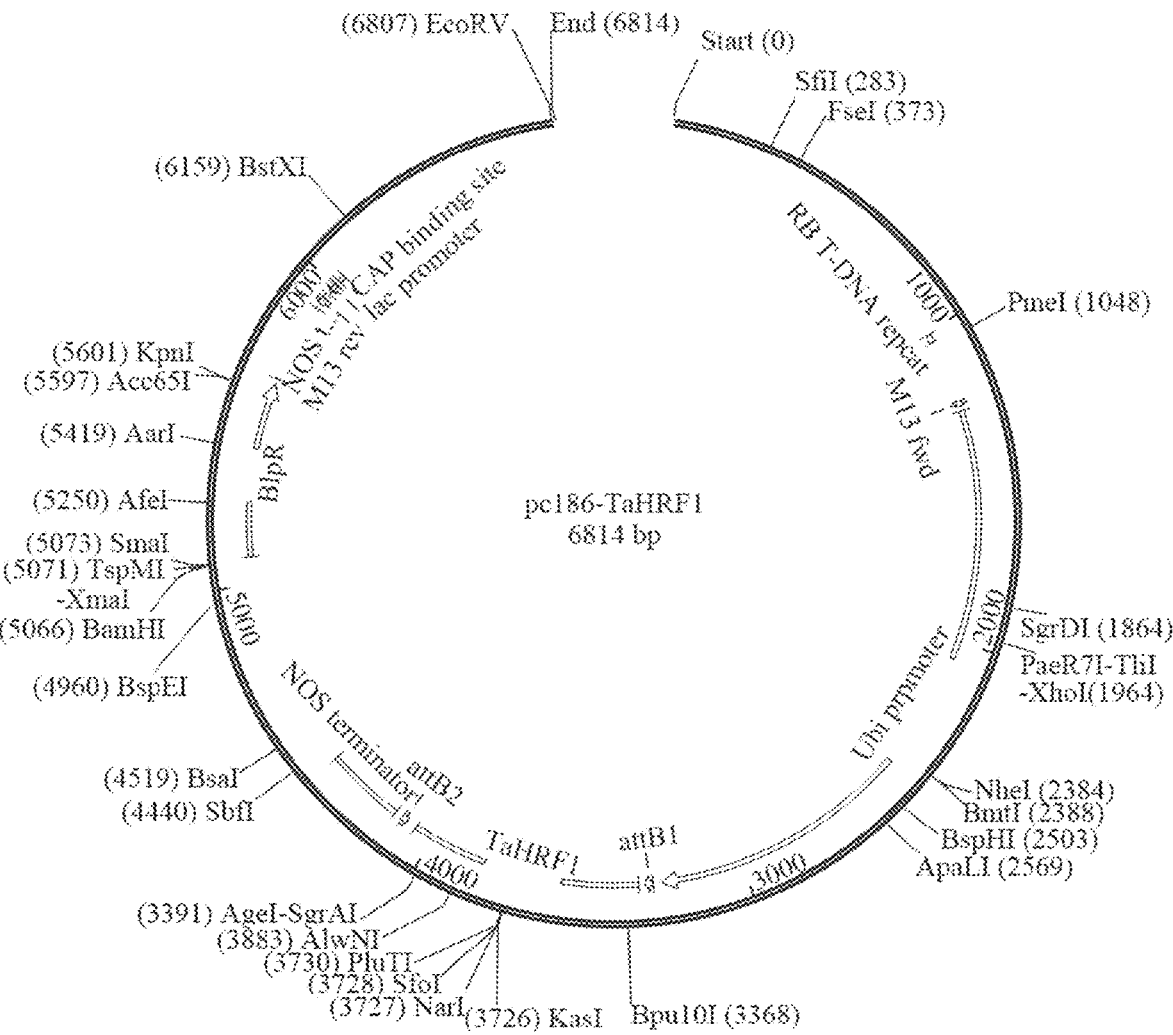
FIG. 1 shows a vector structure diagram of a plant expression vector pc186-TaHRF1.

The amplified PCR product was directionally cloned into a Gateway system by referring to operation steps of a pENTR™ Directional TOPO® Cloning Kit (Thermo Scientific™, catalog number: K2400-20SP), and subsequently sequencing was performed. Monoclonal colonies with correct sequencing were ligated into a pc186 expression vector by an LR reaction to obtain a pc186-TaHRF1 vector. The structure of the vector is as shown in FIG. 1.

The pc186-TaHRF1 was transformed into an *Agrobacterium* EHA105 competent cell, and an *Agrobacterium* strain available for transformation was obtained, which was named pc186-TaHRF1/EHA105.

Example 2: Construction of a Control Vector pc186-GUS

Taking nucleotides at positions 15108-16919 of Sequence ID: MN266288.1 on the NCBI website (www.ncbi.nlm.nih.gov/) as a template, PCR amplification was performed using a primer pair (upstream primer: 5'-ATGT-TACGTCCTGTAGAA-3', SEQ ID NO. 6; downstream primer: 5'-TCATTGTTTGCCTCCCTG-3', SEQ ID NO. 7). An amplification system included 2 μl of upstream primer (10 μmol/μl), 2 μl of downstream primer (10 μmol/μl), 12.5 μl of 2× Phanta Max Master Mix, 1 μl of cDNA template (100-200 ng/μl), and 7.5 μl of ddH₂O. Amplification conditions were: predenaturation at 95° C. for 3 minutes; denaturation at 95° C. for 15 seconds, annealing at 58° C. for 15 seconds, extension at 72° C. for 50 seconds, for 32 cycles of denaturation, annealing and extension; extension at 72° C. for 5 minutes; holding at 16° C.

The amplified PCR product was ligated to a cloning vector Blunt3 by referring to operation steps of a pEASY®-Blunt3 Cloning Kit (catalog number: CB301-01, TransGen Biotech Co., Ltd., Beijing) to obtain a pEASY-B3-GUS vector, and sequencing was performed.

Upon the sequencing analysis, the gene represented by the PCR product was the GUS gene.

The GUS gene can also be synthesized artificially and ligated into a pEASY-Blunt3 vector to obtain pEASY-Blunt3-GUS.

Taking pEASY-Blunt3-GUS as a template, PCR amplification was performed with a primer pair designed (upstream primer: 5'-CACCATGTTACGTCCTGTAGAA-3', SEQ ID NO. 8; downstream primer: 5'-TCAT-TGTTTGCCTCCCTG-3', SEQ ID NO. 7). An amplification system consisted of 2 μl of upstream primer (10 μmol/μl), 2 μl of downstream primer (10 μmol/μl), 12.5 μl of 2× Phanta Max Master Mix, 1 μl of cDNA template, and a balance of ddH₂O to 25 μl. Amplification conditions were: predenaturation at 95° C. for 3 minutes; denaturation at 95° C. for 15 seconds, annealing at 58° C. for 15 seconds, extension at 72° C. for 50 seconds, for 32 cycles; extension at 72° C. for 5 minutes.

Figure 2:
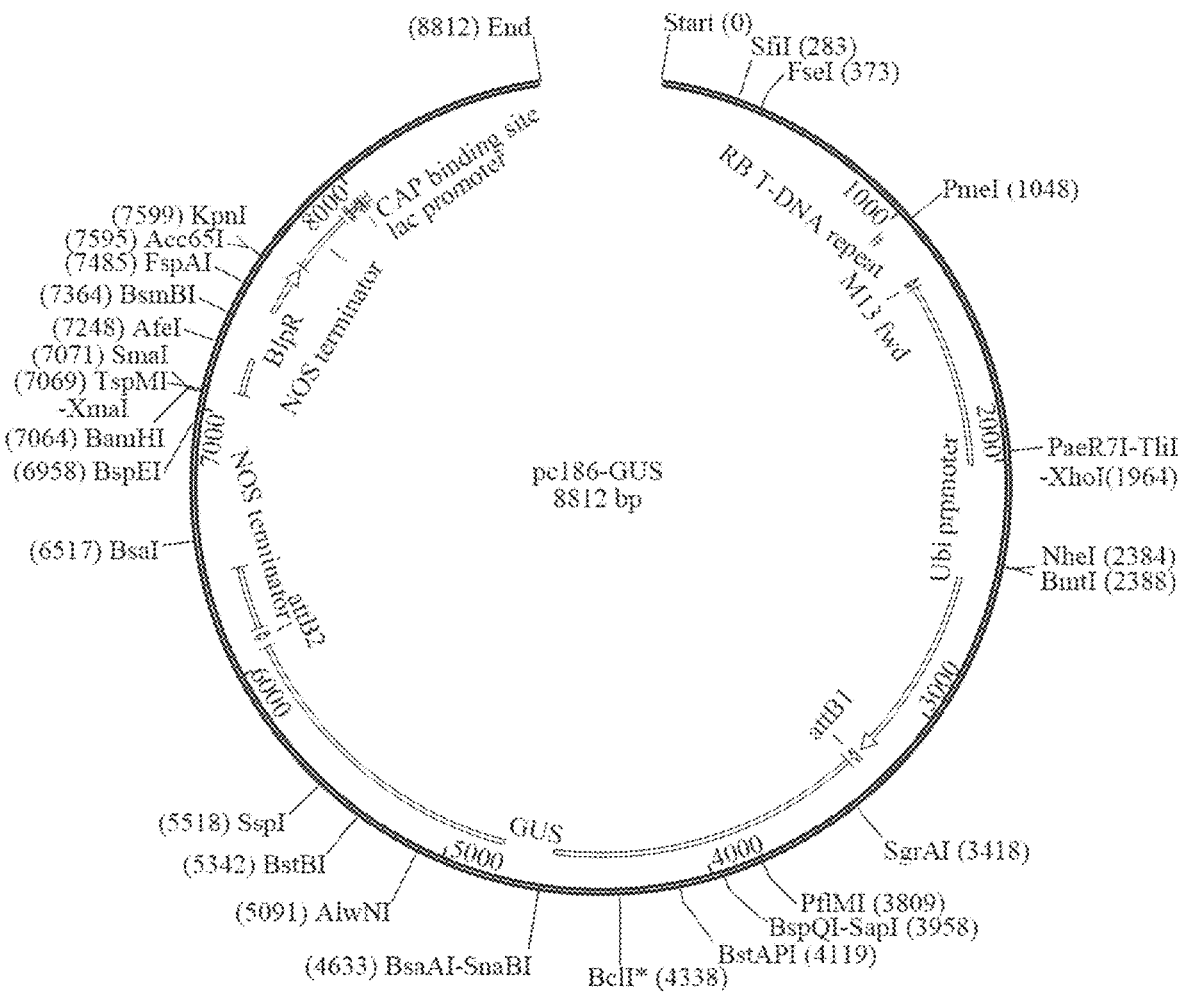
FIG. 2 shows a vector structure diagram of a plant expression vector pc186-GUS.
Figure 3A:
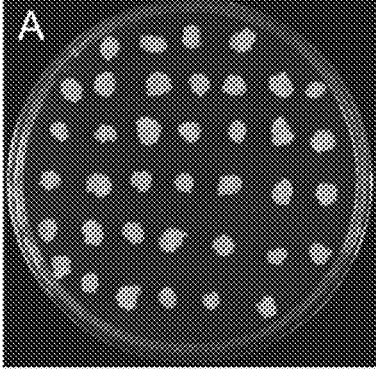
FIGS. 3A-3D shows the tissue culture process of obtaining resistant seedlings by infecting immature embryo of a wheat variety Liangxing 66 with a plant expression vector pc186-TaHRF1 and a control vector pc186-GUS.
Figure 3B:
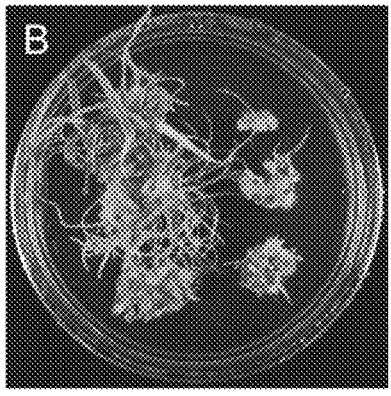
Figure 3C:
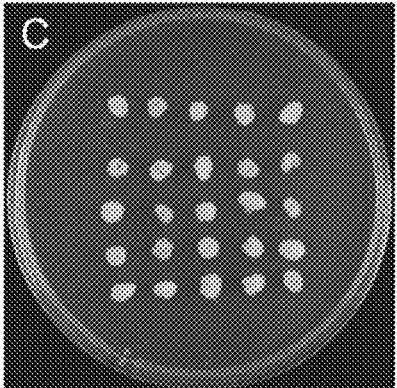
Figure 3D:
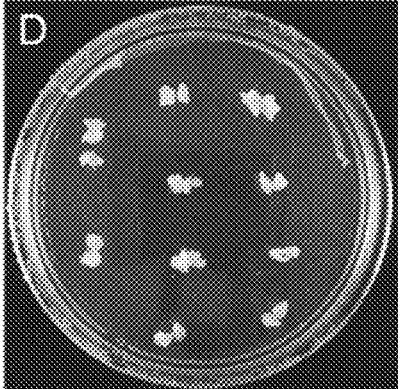
Figure 4A:
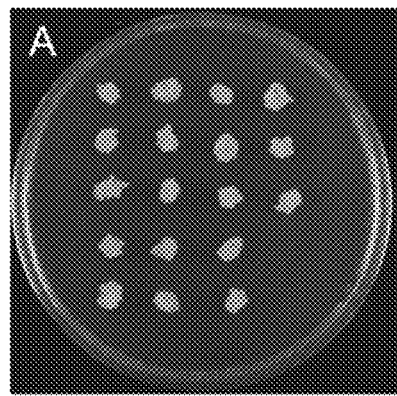
FIGS. 4A-4D shows the tissue culture process of obtaining resistant seedlings by infecting immature embryos of a wheat variety Aifeng 3 with a plant expression vector pc186-TaHRF1 and a control vector pc186-GUS.
Figure 4B:
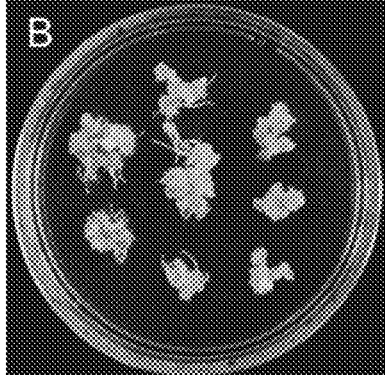
Figure 4C:
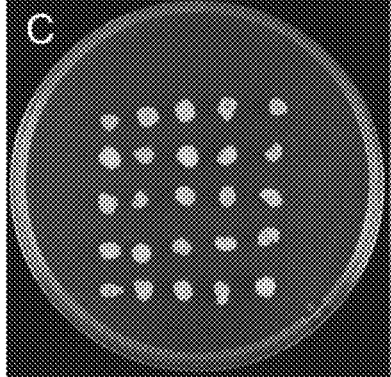
Figure 4D:
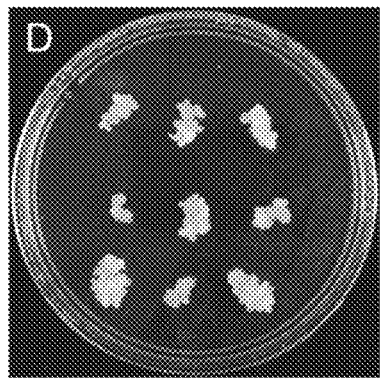

The amplified PCR product was ligated by referring to a pENTR™ Directional TOPO® Cloning Kit (catalog number: K2400-20SP, Thermo Scientific™), and then sequencing procedure was performed. Monoclonal colonies with correct sequencing were ligated into a pc186 expression vector by an LR reaction to obtain a pc186-GUS vector. The structure of the vector is as shown in FIG. 2.

The pc186-GUS was transformed into an *Agrobacterium* EHA105 competent cell, and an *Agrobacterium* strain available for transformation was obtained, which was named pc186-GUS/EHA105.

Example 3: *Agrobacterium*-Mediated Transformation of Wheat Immature Embryo and Identification of Transgenic Plants I. The method of Ishida et al. (Ishida et al., 2015) was referred to for the detailed steps and procedures of the *Agrobacterium*-mediated method of wheat immature embryos. The components of the media are shown in Table 1.

1. Three days before infection, the *Agrobacterium* strains pc186-TaHRF1/EHA105 and pc186-GUS/EHA105 were separately inoculated on a YEP solid medium containing 50 mg/L kanamycin and 50 mg/L rifampicin, and cultured in an incubator at 28° C. in the dark for 2 days. Single colony was picked and inoculated in a YEP liquid medium containing 50 mg/L kanamycin and 50 mg/L rifampicin, and cultured at 28° C. with overnight shaking at 220 rpm. The above *Agrobacterium* solutions were placed in 2 ml sterile centrifuge tubes, and centrifuged at 6000 rpm for 5 minutes. The supernatants were discarded. The precipitates were resuspended with a resuspension buffer to obtain *Agrobacterium* resuspensions of pc186-TaHRF1/EHA105 and pc186-GUS/EHA105, respectively.

2. Immature embryos (with scutellum length of about 2 mm) of different genotypes of wheat 2 weeks after anthesis were collected and infected with *Agrobacterium* resuspensions of pc186-TaHRF1/EHA105 and pc186-GUS/EHA105, respectively. The infected immature embryos were placed with the scutellum side facing up on a WLS-AS medium and cultured in an incubator 23° C. in the dark for 2 days.

3. The co-cultured immature embryos were transferred to a WLS-Res medium and cultured in an incubator at 25° C. in the dark for 5 days.

4. A resulting calli after the recovery culture were transferred to a WLS-P5 medium and cultured in an incubator at 25° C. in the dark for 2 weeks.

5. A resulting calli were then transferred to a WLS-P10 medium and cultured in an incubator at 25° C. in the dark for 3 weeks.

6. A resulting calli were transferred to an LSZ-P5 medium and cultured in an incubator at 25° C. under light conditions for 2 weeks (FIGS. 3A-D and 4A-D).

7. A resulting regenerated resistant shoots of wheat were transferred to an LSF-P5 medium and cultured in an incubator at 25° C. under light conditions until the root length of the regenerated shoots was about 1-2 centimeters.

8. The rooted robust seedlings were transplanted into nutrient soil, and candidate transgenic seedlings of pc186-TaHRF1 and pc186-GUS were obtained.

TABLE 1

Components of media for wheat genetic transformation

| Medium name | Composition |
|---|---|
| WLS-AS | 1/10 MS basal medium, 1/10 MS vitamins, 10 g/L glucose, 100 μM acetosyringone, 8 g/L agarose |
| WLS-Res | MS basal medium, MS vitamins, 0.5 mg/L 2,4-D, 2.2 mg/L picloram, 0.5 g/L glutamine, 0.1 g/L casein, 0.75 g/L MgCl$_2$•6H$_2$O, 40 g/L maltose, 0.85 mg/L AgNO$_3$, 100 mg/L vitamin C, 250 mg/L carbenicillin, 5 g/L agarose |
| WLS-P5 | WLS-Res medium + 5 mg/L phosphinothricin (PPT) |
| WLS-P10 | WLS-Res medium + 10 mg/L PPT |
| LSZ-P5 | MS basal medium, LS vitamins, 5 mg/L zeatin, 20 g/L sucrose, 250 mg/L carbenicillin, 5 mg/L PPT, 3 g/L phytagel |

10

TABLE 1-continued

Components of media for wheat genetic transformation

| Medium name | Composition |
|---|---|
| LSF-P5 | MS basal medium, LS vitamins, 0.2 mg/L IBA, 15 g/L sucrose, 250 mg/L carbenicillin, 5 mg/L PPT, 3 g/L phytagel |

II. PCR Detection of Candidate Transgenic Plants

Genomic DNA was extracted from wheat plants of the T$_0$ generation transformed with the pc186-TaHRF1 and pc186-GUS vectors using a CTAB method (Sambrook and Russell, Molecular Cloning: A Laboratory Manual, 2001).

Taking the extracted genomic DNA of the candidate transgenic plants as a template, PCR amplification was performed with primers designed (upstream primer: 5'-GGCGGTCTGCACCATCGTCAACCACTAC-3', SEQ ID NO. 9; downstream primer: 5'-AGTCCAGCTGCCAGAAACCCACGTCATG-3', SEQ ID NO. 10), so as to detect the presence or absence of a bar gene. If the bar gene is present, the length of the amplified fragment is 446 bp. An amplification system had a total volume of 20 μl, and included 1 μl of upstream primer (10 μmol/μl), 1 μl of downstream primer (10 μmol/μl), 10 μl of 2× Rapid Taq Master Mix, 1 μl of genomic DNA template (100-200 ng/μl), and 7 μl of ddH$_2$O. Amplification conditions were: predenaturation at 95° C. for 3 minutes; denaturation at 95° C. for 15 seconds, annealing at 58° C. for 15 seconds, extension at 72° C. for 15 seconds, for 32 cycles of denaturation, annealing and extension; extension at 72° C. for 5 minutes.

Figure 5:
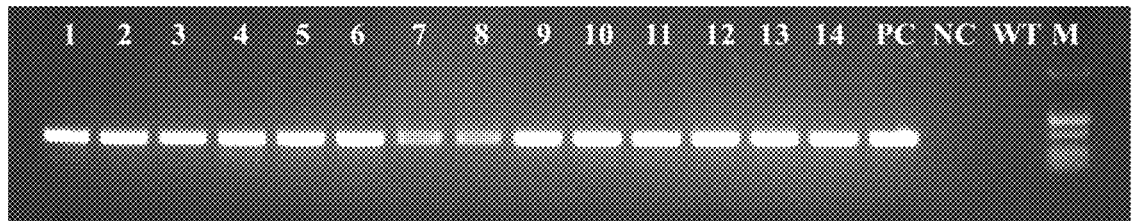
FIG. 5 shows the results of PCR-specific amplification of a bar gene in candidate transgenic plants obtained by transforming a plant expression vector pc186-TaHRF1. In the figure, 1-8 represent candidate transgenic plants of Liangx-

The PCR identification results are shown in FIG. 5. There was no bar gene fragment with a length of 446 bp in wild-type wheat.

III. Statistics of Transformation Efficiency of Different Genotypes of Wheat

After immature embryos of wheat 14-15 days after anthesis were infected with *Agrobacterium*, the induced calli were screened. When they were transferred to the LSF-P5 medium, the number of induced calli was counted. After PCR identification, the number of transgenic positive seedlings was counted. Finally, the callus induction efficiency and the transformation efficiency were calculated according to the following formulas:

callus induction efficiency (%)=(number of calli÷total number of immature embryos)× 100%;

transformation efficiency (%)=(number of positive seedlings÷total number of immature embryos)× 100%;

The transformation of the pc186-TaHRF1 vector could effectively boost the transformation efficiency of wheat compared with the control vector pc186-GUS. The results are as shown in Table 2.

TABLE 2

Comparison of transformation efficiency of the control vector pc186-GUS and the pc186-TaHRF1 vector

| Genotype | Vector | Total number of immature embryos | Number of resistant calli | Number of positive seedlings | Callus induction efficiency (%) | Transformation efficiency (%) |
|---|---|---|---|---|---|---|
| Liangxing 66 | pc186-TaHRF1 | 169 | 161 | 77 | 95.27% | 45.56% |
| | pc186-GUS | 135 | 121 | 0 | 89.63% | 0.00% |

TABLE 2-continued

| | | Total number of immature embryos | Number of resistant calli | Number of positive seedlings | Callus induction efficiency (%) | Transformation efficiency (%) |
|---|---|---|---|---|---|---|
| Genotype | Vector | | | | | |
| Aifeng 3 | pc186-TaHRF1 | 128 | 117 | 51 | 91.41% | 39.84% |
| | pc186-GUS | 117 | 101 | 0 | 86.32% | 0.00% |

Taking immature embryos of the wheat production and popularization variety Liangxing 66 as explants, after they were transformed with the pc186-TaHRF1 vector and the control vector pc186-GUS by an *Agrobacterium*-mediated method, the callus induction rates were 95.27% and 89.63%, respectively. The transformation efficiency of the pc186-TaHRF1 vector was 45.56%, whereas no transgenic plants could be obtained with the control vector. When genetic transformation was performed using the backbone wheat variety Aifeng 3 as a donor plant, no positive transgenic plants could be obtained with the control vector pc186-GUS, whereas the transformation efficiency of the pc186-TaHRF1 vector was 39.84%. As can be seen from the above results, the TaHRF1 gene could significantly improve the transformation efficiency of wheat and partially solve the problem of genotype dependence in the genetic transformation of wheat.

IV. Investigation of Phenotypes of Transgenic Plants:

The growth and development of positive plants obtained by transforming Fielder with the plant expression vector pc186-TaHRF1 and those of the wild-type Fielder were investigated. The results are shown in FIG. 6. The results showed that the plants with overexpressed TaHRF1 gene grew and developed normally without affecting the agronomic traits of wheat.

The examples described above are only some embodiments of the present application and are not intended to limit the present application. For those skilled in the art, various changes and variations may be made to the present application. Any modification, equivalent, improvement, etc., made within the spirit and principles of the present application, should be encompassed in the scope of protection of the present application.

What is claimed is:

1. A method for boosting genetic transformation efficiency of wheat, comprising:

transforming a TaHRF1 gene and a target nucleic acid molecule into a target plant, wherein the TaHRF1 gene is the nucleic acid molecule of SEQ ID NO: 1 or the nucleic acid molecule encoding the amino acid sequence of SEQ ID NO: 2, excluding SEQ ID NO:1;

wherein the TaHRF1 gene and the target nucleic acid molecule are transferred to the wheat by a pc186 expression vector;

wherein a variety of the wheat is Liangxing 66 or Aifeng 3.

2. The method of claim 1, wherein the protein encoded by the TaHRF1 gene is the protein as shown in any one of (A1) or (A2) below:

(A1) the protein consisting of the amino acid sequence of SEQ ID NO: 2;

(A2) a fusion protein obtained by attaching a protein tag to the N-terminus and/or the C-terminus of the protein defined in (A1).

* * * * *

SEQUENCE LISTING

```
Sequence total quantity: 15
SEQ ID NO: 1               moltype = DNA  length = 729
FEATURE                    Location/Qualifiers
source                     1..729
                           mol_type = other DNA
                           note = Nucleotide sequence of TaHRF1 gene
                           organism = synthetic construct
SEQUENCE: 1
atgccgcaga cgccatcgac ccgttggtgc ccgacgcctg agcagctgat gatcctggag  60
gagatgtacc ggagcggcgt gcgcacacct aacgcggcgg agatccagca gatcacggcg  120
cacctcgcct actacggccg catcgaggga aagaacgtct tctactggtt ccagaaccac  180
aaggcccgcg agcgccagcg tctccgtcgc cgcctctgcg cccgccacca gcaaccctcc  240
tccccggcgg ctcctcctcc tcctcctcct cctcatactg gtgctgccgg tggcggaggc  300
aatgctgctg gtgctggtgc gggcgtgaac gtgatgcacc ccgcggtgat gcagctgcac  360
catcaccacc acacatacgc taccagctgc ttcatggcgc ctcagggcta cttggagcag  420
gaaacagcag cagcaggagc tcttccagtt tcggggttgg agtttgcagg caagacaagc  480
cagcagcagg aatggatggc gcaggagcag atggtgatgg agaacagcaa cattaacaac  540
agtgtagcag cagctggagg cagctccgca tcggccggcg gtggtatgaa taatatgacc  600
ccgccgccat ggccatgctg ccggccgctc agaaccctag agctcttccc tacaaagagc  660
accggtggcg gcctcaggga cgagtgcagc agctccaagt cctcctcttg ctccacctcc  720
acaaactag                                                          729

SEQ ID NO: 2               moltype = AA  length = 242
FEATURE                    Location/Qualifiers
source                     1..242
                           mol_type = protein
                           note = Amino acid sequence of protein TaHRF1
                           organism = synthetic construct
SEQUENCE: 2
MPQTPSTRWC PTPEQLMILE EMYRSGVRTP NAAEIQQITA HLAYYGRIEG KNVFYWFQNH  60
KARERQRLRR RLCARHQQPS SPAAPPPPPP PHTGAAGGGG NAAGAGAGVN VMHPAVMQLH  120
HHHHTYATSC FMAPQGYLEQ ETAAAGALPV SGLEFAGKTS QQQEWMAQEQ MVMENSNINN  180
SVAAAGGSSA SAGGGMNNMT PPPWPCCRPL RTLELFPTKS TGGGLRDECS SSKSSSCSTS  240
TN                                                                 242

SEQ ID NO: 3               moltype = DNA  length = 20
FEATURE                    Location/Qualifiers
source                     1..20
                           mol_type = other DNA
                           note = Upstream primer of a cDNA
                           organism = synthetic construct
```

-continued

```
SEQUENCE: 3
atgccgcaga cgccatcgac                                                    20

SEQ ID NO: 4              moltype = DNA  length = 22
FEATURE                   Location/Qualifiers
source                    1..22
                          mol_type = other DNA
                          note = Downstream primer of a cDNA
                          organism = synthetic construct
SEQUENCE: 4
ctagtttgtg gaggtggagc aa                                                 22

SEQ ID NO: 5              moltype = DNA  length = 21
FEATURE                   Location/Qualifiers
source                    1..21
                          mol_type = other DNA
                          note = Upstream primer of pEASY-Blunt3-TaHRF1
                          organism = synthetic construct
SEQUENCE: 5
caccatgccg cagacgccat c                                                  21

SEQ ID NO: 6              moltype = DNA  length = 18
FEATURE                   Location/Qualifiers
source                    1..18
                          mol_type = other DNA
                          note = Upstream primer of nucleotides at positions
                           15108-16919 of Sequence ID: MN266288.1 on the NCBI website
                          organism = synthetic construct
SEQUENCE: 6
atgttacgtc ctgtagaa                                                      18

SEQ ID NO: 7              moltype = DNA  length = 18
FEATURE                   Location/Qualifiers
source                    1..18
                          mol_type = other DNA
                          note = Downstream primer of nucleotides at positions
                           15108-16919 of Sequence ID: MN266288.1 on the NCBI website
                          organism = synthetic construct
SEQUENCE: 7
tcattgtttg cctccctg                                                      18

SEQ ID NO: 8              moltype = DNA  length = 22
FEATURE                   Location/Qualifiers
source                    1..22
                          mol_type = other DNA
                          note = Upstream primer of pEASY-Blunt3-GUS
                          organism = synthetic construct
SEQUENCE: 8
caccatgtta cgtcctgtag aa                                                 22

SEQ ID NO: 9              moltype = DNA  length = 28
FEATURE                   Location/Qualifiers
source                    1..28
                          mol_type = other DNA
                          note = Upstream primer of extracted genomic DNA of the
                           candidate transgenic plants
                          organism = synthetic construct
SEQUENCE: 9
ggcggtctgc accatcgtca accactac                                          28

SEQ ID NO: 10             moltype = DNA  length = 28
FEATURE                   Location/Qualifiers
source                    1..28
                          mol_type = other DNA
                          note = Downstream primer of extracted genomic DNA of the
                           candidate transgenic plants
                          organism = synthetic construct
SEQUENCE: 10
agtccagctg ccagaaaccc acgtcatg                                          28

SEQ ID NO: 11             moltype = AA  length = 6
FEATURE                   Location/Qualifiers
source                    1..6
                          mol_type = protein
                          note = Amino acid sequence of tag Poly-Arg
                          organism = synthetic construct
SEQUENCE: 11
RRRRRR                                                                    6
```

-continued

```
SEQ ID NO: 12          moltype = AA   length = 6
FEATURE                Location/Qualifiers
source                 1..6
                       mol_type = protein
                       note = Amino acid of tag Poly-His
                       organism = synthetic construct
SEQUENCE: 12
HHHHHH                                                          6

SEQ ID NO: 13          moltype = AA   length = 8
FEATURE                Location/Qualifiers
source                 1..8
                       mol_type = protein
                       note = Amino acid of tag FLAG
                       organism = synthetic construct
SEQUENCE: 13
DYKDDDDK                                                        8

SEQ ID NO: 14          moltype = AA   length = 8
FEATURE                Location/Qualifiers
source                 1..8
                       mol_type = protein
                       note = Amino acid of tag Strep-tag II
                       organism = synthetic construct
SEQUENCE: 14
WSHPQFEK                                                        8

SEQ ID NO: 15          moltype = AA   length = 10
FEATURE                Location/Qualifiers
source                 1..10
                       mol_type = protein
                       note = Amino acid of tag c-Myc
                       organism = synthetic construct
SEQUENCE: 15
EQKLISEEDL                                                      10
```